United States Patent
Salmon-Legagneur et al.

(10) Patent No.: US 12,327,205 B2
(45) Date of Patent: Jun. 10, 2025

(54) SYSTEM FOR DETERMINING A FLIGHT REST SCENARIO FOR AN AIRCRAFT CREW

(71) Applicant: DASSAULT AVIATION, Paris (FR)

(72) Inventors: François Salmon-Legagneur, Saint Cloud (FR); Jean-Christophe Denjean, Merignac (FR); Valentin Ligier, Saint-Cloud (FR); Astrid Michon, Saint Cloud (FR)

(73) Assignee: DASSAULT AVIATION, Paris (FR)

( * ) Notice: Subject to any disclaimer, the term of this patent is extended or adjusted under 35 U.S.C. 154(b) by 98 days.

(21) Appl. No.: 17/586,242

(22) Filed: Jan. 27, 2022

(65) Prior Publication Data
US 2022/0245537 A1     Aug. 4, 2022

(30) Foreign Application Priority Data

Feb. 1, 2021 (FR) ................................ FR 21 00938

(51) Int. Cl.
*G06Q 10/0631* (2023.01)
*G06F 3/04847* (2022.01)
*G06Q 10/067* (2023.01)
*G06Q 10/1093* (2023.01)

(52) U.S. Cl.
CPC ... *G06Q 10/06311* (2013.01); *G06F 3/04847* (2013.01); *G06Q 10/067* (2013.01); *G06Q 10/1093* (2013.01)

(58) Field of Classification Search
CPC ............. G06Q 10/067; G06Q 10/1093; G06Q 10/06398; G06Q 10/06311; G06F 3/04847; G16H 50/50
See application file for complete search history.

(56) References Cited

U.S. PATENT DOCUMENTS

| | | |
|---|---|---|
| 2005/0154634 A1 | 7/2005 | Konop |
| 2010/0030406 A1* | 2/2010 | Christophe ............ B64D 47/02 244/118.6 |
| 2011/0071873 A1 | 3/2011 | Vaughan et al. |

(Continued)

FOREIGN PATENT DOCUMENTS

WO   WO-2012015383 A1 *  2/2012  ............. G06Q 10/06

OTHER PUBLICATIONS

Search Report for priority application FR 21 00938.
(Continued)

*Primary Examiner* — Charles Guiliano
(74) *Attorney, Agent, or Firm* — Davidson Kappel LLC

(57) ABSTRACT

A system is (10) for determining a flight rest scenario for an aircraft crew (12) comprising at least two pilots able to fly the aircraft (12) during a flight. The system (10) comprises a display device (16) comprising a screen (20), a module (32) for acquiring flight context and constraints inputs, and a module (34) for determining at least one crew rest scenario for the flight from the acquired inputs. The determination module (34) is able to determine the rest scenario from at least one simulation by a biomathematical fatigue model having at least one of the acquired inputs as variables. The system also includes a display management module (36) configured to display the determined rest scenario on the screen (20) of the display device (16).

25 Claims, 4 Drawing Sheets

(56) References Cited

U.S. PATENT DOCUMENTS

2012/0029971 A1* 2/2012 Lee ................... G06Q 10/06
705/7.28
2020/0290740 A1* 9/2020 Rangan ............... G06V 20/597

OTHER PUBLICATIONS

Sun Ruishan et al: "Study on a Model of Flight Fatigue Dynamic Risk Index", Jun. 22, 2014, Advances in Biometrics: Advances in Biometrics: International Conference, ICB 2007, Aug. 27-29, 2007, p. 357 to 386.

* cited by examiner

SYSTEM FOR DETERMINING A FLIGHT REST SCENARIO FOR AN AIRCRAFT CREW

The present disclosure relates to a system for determining an in-flight rest scenario for a crew of an aircraft.

BACKGROUND

Fatigue and the increased time awake during flight are known to affect an individual's performance. This makes the likelihood of errors being made and incidents occurring more probable. In order to counteract this tendency, pilots can take advantage of rest periods while certain flights are cruising (during flights involving extra crew, for example). This makes it possible for pilots to alternate between cockpit duty and rest periods during the cruise period.

Usually, operationally, the crew determines the rest period distribution between the pilots during the cruise period by mutual agreement. The captain remains responsible for organizing this, and may also give the choice of rest period to the pilot who will be responsible for the aircraft descent and landing at the end of the flight.

In addition, if one of the pilots in the crew becomes too tired during the flight, aviation regulations may allow the pilot to take a nap that was not initially planned.

SUMMARY

However, these usual approaches are unsatisfactory. Indeed, they are approximate and do not systematically ensure the optimization of the pilot fatigue level during flight. These known approaches can therefore pose a risk to the safety of the aircraft during flight.

One object of the present disclosure is therefore to provide a system for improving the safety of the aircraft by minimizing pilot fatigue during flight.

To this end, it is an object of the present disclosure to provide a system for determining an in-flight rest scenario for a crew of an aircraft, the crew comprising at least two pilots able to fly the aircraft during a flight of the aircraft, the system comprising:
- a display device comprising a screen,
- a module for acquiring flight context and constraints inputs,
- a module for determining at least one in-flight rest scenario for the crew from said acquired inputs, the determination module being able to determine said rest scenario from at least one simulation by a biomathematical fatigue model, having at least one of said acquired inputs as variables,
- a display management module, configured to display the determined rest scenario on the display device screen.

The system according to the present disclosure makes it possible to optimize the in-flight rest of an aircraft crew and to minimize its fatigue state during the operation.

The system according to the present disclosure may comprise one or more of the following features, taken alone or in any technically possible combination:
- the rest scenario is determined for a cruise phase of flight and comprises a rest period(s) chronology, with each rest period being assigned to one of the pilots, and the flight context and constraint inputs comprise at least one piloting constraint by the aircraft crew, the determination module being configured to determine at least one chronology of rest period(s) compatible with each piloting constraint, the determination module being configured to simulate and determine at least one fatigue level of each pilot for each compatible chronology, by the biomathematical model, the determination module being configured to classify each compatible chronology according to an order relationship established from the simulated fatigue levels, the determined rest scenario comprising the compatible chronology that has the best classification according to said order relationship;
- the or one of the piloting constraints is a minimum number of pilot(s) required on duty at each moment of the cruise phase; and/or the or one of the piloting constraints is a predetermined temporal or geographical area of flight requiring a predetermined number of pilots on duty, the predetermined number being the totality of pilots in the crew, for example; and/or the or one of the piloting constraints is a temporal or geographical area of flight requiring one predetermined pilot on duty, from among the crew pilots; and/or the or one of the piloting constraints is a parameter representing a tolerance to a current meteorological flight context;
- the flight context and constraints inputs comprise at least one pre-flight fatigue parameter for each pilot, representing a pre-flight fatigue state reported by the pilot, the biomathematical model having said pre-flight fatigue parameter as a variable;
- the determination module is configured for the biomathematical model to simulate and determine, for each compatible chronology, a maximum fatigue level of each pilot on duty during each other pilot's rest period and/or a fatigue level at a calculated top of aircraft descent time, of at least each pilot scheduled to be on duty at said moment, the order relationship being established on at least one of said simulated and determined fatigue levels;
- the flight context and constraint inputs include an available cruise time, a number of required crew rest period(s) to be provided for the crew and a rest period duration, the determination module being configured to discretize the available cruise time into a plurality of discretized moments, the discretization being done with a predetermined discretized timestep, the determination module being configured to determine each compatible chronology so that each rest period of the compatible chronology has a start time corresponding to one of the discretized moments;
- after discretization, the determination module is configured to list all the chronologies of rest period in which each rest period has a start time corresponding to one of the discretized moments, and to verify, for each listed chronology, whether the listed chronology is compatible with each piloting constraint;
- after having determined the compatible chronology with the best classification, the determination module is configured to determine, for each period of said chronology, a time window including the rest period, the determination module being configured to discretize, with a reduced discretized timestep, each time window into a plurality of reduced discretized moments, the reduced discretized timestep being smaller than the predetermined discretized timestep, the determination module being configured, after the reduced discretization, to list all the new chronologies of rest periods in which each rest period has a start time corresponding to one of the reduced discretized moments and to verify, for each listed new chronology, whether the listed new chronology is compatible with each piloting constraint, the determination module being configured to simulate and determine, by the biomathematical model and for each new compatible chronology, at least one new fatigue level of each pilot, the determination module being configured to classify each new compatible chronology, according to the order relationship, established from the simulated new fatigue levels, the determined rest scenario comprising the new compatible chronology having the best classification according to said order relationship;

before determining each chronology of rest period(s) compatible with each acquired piloting constraint, the determination module is configured to verify at least one compliance condition between at least two of the acquired inputs, and configured to modify one of the acquired inputs if the compliance condition between inputs is unverified and/or to generate an alert for the crew if the input compliance condition is not verified, with the display management module configured to generate a graphical representation of the alert;

the flight context and constraint inputs comprise an available cruise time, a number of necessary crew rest periods to be provided, and a rest period duration; the determination module being configured to verify a compliance condition between the available cruise time and the rest periods to be scheduled, the compliance condition being that the available cruise time is long enough to include each rest period, the determination module preferably being configured to generate an alert to the crew if the available cruise time is too short to include each rest period and/or configured to reduce the duration of at least one of the rest periods to be scheduled if the available cruise time is too short to include each rest period;

each rest period comprises an authorized sleep duration and a shift transition duration;

the determined rest scenario also comprises duty periods for each pilot, the determination module being configured to simulate and determine, by the biomathematical model, each pilot's fatigue level evolution over each pilot's duty period, the display management module being configured to display a specific graphical representation of the determined rest scenario representing each evolution on the display device screen;

the determination system comprises a human/machine interface and the display management module is configured to display a window on the display device screen comprising a plurality of graphic input acquisition areas, each graphic input acquisition area being associated with at least one of the flight context and constraint inputs, with the acquisition module configured to acquire at least some of the flight context and constraint inputs by activating graphical elements displayed in each acquisition area, the action being implemented via the human/machine interface;

the determination system comprises a human/machine interface and said display management module is configured to detect an action of modifying the displayed rest scenario implemented by an operator through the human/machine interface, the determination module being adapted to simulate and determine each pilot's fatigue level from the biomathematical fatigue model in the modified rest scenario, with the display management module configured to display the modified rest scenario according to a specific graphical representation;

said action of modifying the displayed rest scenario comprises modifying a temporal position of at least one of the rest periods of the determined scenario and/or adding a new rest period and/or deleting one of the rest periods;

the flight context and constraint inputs may include a post-flight rest parameter for each pilot representing a rest option for the pilot after landing the aircraft and before any further take-off, with the order relationship also established based on said post-flight rest parameters;

the determination module is configured to determine the rest scenario before and/or during a flight of the aircraft;

the discretized timestep is determined by the determination module on the basis of calculation constraint parameters, with the calculation constraint parameters preferably comprising a maximum calculation duration, an estimated calculation duration per chronology, a number of rest period(s) to be provided, a duration of each rest period and an available cruise time;

the available cruise time corresponds to the difference between a calculated aircraft top of climb time and a calculated aircraft top of descent time or the difference between a current flight time and a calculated top of descent time of the aircraft; and the display management module is configured to further display at least one alternative rest scenario, the alternative rest scenario comprising the compatible chronology that has the second best classification according to the order relationship.

The present disclosure also relates to an aircraft comprising the system for determining a flight rest scenario as described above.

The aircraft may comprise one or more of the following features, taken alone or in any technically feasible combination:

the aircraft comprises at least one on-board system, the determination system being connected to the on-board system, the determination system being configured to send a signal representing the determined rest scenario to the on-board system;

the onboard system is a printer or an avionics system; and the onboard system comprises a device for awaking a pilot at rest and a wake-up module connected to said determination system configured to operate the wake-up device based on the determined rest scenario.

The present disclosure also relates to a method for determining an in-flight rest scenario for a crew of an aircraft, the crew comprising at least two pilots able to fly the aircraft during a flight of the aircraft, the method comprising the following steps:

acquiring flight context and constraints inputs, determining at least one in-flight rest scenario for the crew from said acquired inputs, said rest scenario being determined from at least one simulation by a biomathematical fatigue model, having at least one of said acquired inputs as variables, and displaying the determined rest scenario on a screen of a display device.

BRIEF SUMMARY OF THE DRAWINGS

The present disclosure will be better understood upon reading the following description, given only by way of example, and made with reference to the appended drawings, in which.

DETAILED DESCRIPTION

Figure 1:
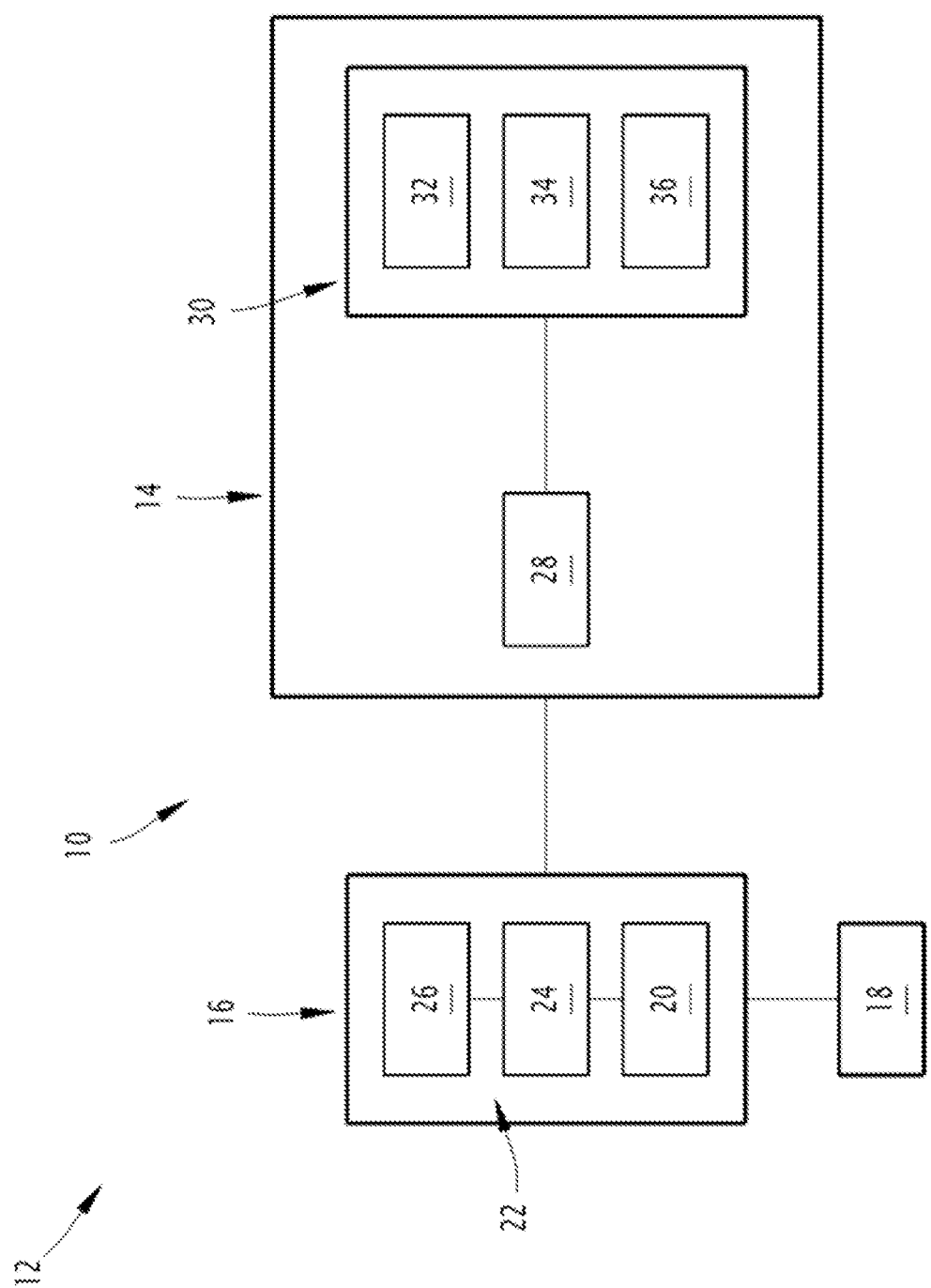
FIG. 1 is a schematic flowchart of a determination system according to an example embodiment of the present disclosure.

A system 10 for determining a flight rest scenario of an aircraft crew 12 according to an embodiment of the present disclosure is illustrated in FIG. 1.

The aircraft 12 comprises at least one on-board system such as a printer and/or avionics system.

The crew comprises at least two pilots able to fly the aircraft 12 during a flight of the aircraft 12.

In particular, the crew comprises more pilots than are strictly necessary to fly the aircraft 12, and at least one of said pilots may be off duty while the other pilot(s) are on duty during a flight, according to the rules defined by each airline.

Here and hereafter, "pilot on duty" is defined as a pilot who performs the professional activities associated with his/her position during a given duty period. For example, a pilot on duty is at the controls of the aircraft 12 in the cockpit.

For example, the system 10 is comprised in the aircraft 12.

The system 10 includes a processing unit 14, a display device 16, and a human/machine interface 18.

The system 10 is preferably connected to said onboard system of the aircraft 12.

The display device 16 is preferably located in the cockpit of the aircraft 12.

The display device 16 comprises a screen 20.

The display device 16 also comprises graphic data processing means 22 such as a graphics processor 24 and associated graphics memory 26.

The graphics processor 24 is adapted to process the graphics data stored in the graphics memory 26 and to display that data or a representation thereof on the screen 20.

The human/machine interface 18 is able to allow the crew to interact with the processing unit 14 and/or the display device 16, as described below.

The human/machine interface 18 comprises a control device such as a touch control device, configured to detect the position on a surface of this control device of one or more members, hereinafter referred to as control members. In a known way, these control members can be a stylus or an operator's fingers.

In the following description, a preferred embodiment will be considered in which this touch control device and the screen 20 have a common shape, in the form of a touch screen. Thus, the human/machine interface 18 is configured to detect the position of one or more control members on the surface of the screen 20.

The processing unit 14 is adapted to execute applications necessary for the operation of the determination system 10.

To this end, the processing unit 14 comprises a processor 28 and at least one memory 30.

The processor 28 is adapted to execute applications contained in the memory 30, preferably an operating system for conventional computer system operations.

The processing unit 14 thus comprises at least one module 32 for acquiring flight context inputs and constraints and a module 34 for determining at least one in-flight rest scenario for the crew of the aircraft 12 from said acquired inputs.

The processing unit 14 also comprises a display management module 36 configured to display the determined rest scenario on the screen 20 of the display device 16.

Said modules 32, 34, 36 are stored in the memory 30, for example, and are suitable for execution by the processor 28 to implement the functions described below. In a variant, each module 32, 34, 36 is implemented in the form of programmable logic components or dedicated integrated circuits intended to perform the functions described below.

In a preferred embodiment, the acquisition module 32 is able to acquire inputs through the human/machine interface 18 by interrogation of the memory 30 and/or through sensors of the aircraft 12.

Once the inputs are acquired, the acquisition module 32 is able to store them in the memory 30, for example.

Various examples of flight context inputs and constraints suitable for acquisition by the acquisition module 32 will now be described.

The flight context and constraint inputs include at least the number of pilots in the crew, for example, and, preferably, characteristic information associated to each pilot.

The characteristic information is stored in the memory 30 and/or is acquired by being entered by a crew member via the human/machine interface 18.

The characteristic information may comprise the age of the pilot and the hierarchical status of the pilot within the crew, for example. For example, one of the pilots has the status of captain of the crew as a hierarchical status.

The characteristic information also comprises a pilot identifier such as the pilot's name, for example.

Thus, the determination system 10 is flexible vis-a-vis the crew composition.

The flight context and constraint inputs also include a predetermined rest period duration.

The rest period duration is acquired by being entered by a crew member via the human/machine interface 18, for example.

The rest period duration is the same for each rest period determined, for example.

In particular, the rest period duration comprises an authorized sleep duration followed by a predetermined shift transition duration. As explained in more detail below, the rest period duration is entered manually by one of the pilots, for example.

The shift transition time is defined as a time period prior to returning to duty during which the pilot is prepared for return to duty, for example by another pilot on duty.

The authorized sleep time and shift transition time are acquired by being input by a crew member via the human/machine interface 18, for example.

The flight context and constraint inputs also comprise a number of required crew rest period(s) to be provided.

The number of required crew rest period(s) to be provided is determined based on a number of pilot(s) for which a rest period is to be provided and a number of rest period(s) for each pilot, for example.

The number of rest periods is acquired by being entered by a crew member via the human/machine interface 18, for example.

The number of rest periods for each pilot is not necessarily the same for all pilots in the crew.

This is the case when determination of the rest scenario is carried out during the flight and at least one of the pilots has already had at least one rest period, for example. The number of rest periods to be planned for at least one of the pilots can be zero in this case, for example, with the pilot then not authorized to rest during the remainder of the flight.

The flight context and constraint inputs also include flight-associated information.

The memory 30 stores a plurality of flights and information associated to each stored flight, for example.

Each flight comprises at least a takeoff climb phase, a cruise phase, and a descent for landing phase. The cruise phase is particularly defined as the phase of flight between top of climb and top of descent. The cruise phase includes at least one cruise altitude (also called flight level).

The top of climb, also called TOC, is the calculated transition from the climb phase to the cruise phase of flight, the point at which the planned climb to a cruise altitude is completed.

The top of descent, also called TOD, is the calculated transition from a cruise phase of flight to the descent phase, or the point at which the planned descent to a final approach altitude is initiated.

Advantageously, the information relating to the flight of the aircraft 12 includes a calculated top of climb time and a calculated top of descent time of the aircraft 12 for the flight.

The information relating to the flight of the aircraft 12 also comprises at least one calculated takeoff time and one calculated landing time.

Each of these calculated times is preferably initially calculated, i.e. prior to the flight, based on a flight plan of the aircraft 12 stored in the memory 30.

Each of these calculated times is preferably updated multiple times during the flight of the aircraft 12 based on the current position of the aircraft 12 at that time, the capabilities of the aircraft 12 and the weather conditions.

Among the information relating to the flight of the aircraft 12, the flight context and constraints inputs also include an available cruise time.

As discussed below, the determination module 34 is configured to be triggered to determine the rest scenario in advance of and/or during the flight of the aircraft 12.

Thus, when occurring before the cruise phase, the available cruise time corresponds to the difference between the calculated top of climb time of the aircraft 12 and the calculated top of descent time of the aircraft 12, for example. In a variant, when the current time occurs during the cruise phase, the available cruise time is the difference between a current flight time and the calculated top of descent time of the aircraft 12, for example.

Other information associated to the flight of the aircraft 12 also includes events intended to occur during the flight, for example. The events include, for example:
- flights by the aircraft 12 over predefined waypoints in accordance with the flight plan,
- scheduled radio communications between the crew and an external control authority,
- the initiation of procedures such as flight level change procedures,
- the occurrence of hazards, climatic hazards in particular, such as passing through areas of strong wind, thunderstorms, or icing conditions,
- specific actions intended to be carried out by at least one of the pilots of the crew, with these actions intended to be carried out at set times during the flight or during flights over predefined waypoints by the aircraft 12, and may include tasks intended to be carried out personally by one of the pilots in the crew.

Each event is associated to information relating to this event in the memory 30. This information includes a fixed or expected time of occurrence of the event, for example. This expected time is initially determined, i.e. before the flight, based on the flight plan of the aircraft 12, and is preferably updated multiple times during the flight of the aircraft 12 based on the position of the aircraft 12 at that time, the capabilities of the aircraft 12 and the weather conditions.

The flight context and constraint inputs include at least one piloting constraint by the crew of the aircraft 12. Advantageously, the inputs include a plurality of piloting constraints by the crew of the aircraft 1212.

In particular, the constraints constrain the piloting of the aircraft 12 by the crew.

Each piloting constraint is acquired by being reported by a crew member via the human/machine interface 18 and/or stored in the memory 30, for example.

Preferably, one of the piloting constraints is a minimum required number of pilot(s) on duty at each point in the cruise phase.

This minimum required number reflects the extent to which different pilots' rest periods may overlap. For example, if there are at least three pilots and a minimum requirement of 1, then overlapping rest periods are possible.

"Overlapping" means that a first rest period overlaps a second rest period, if at least part of the first rest period occurs at the same time as at least part of the second rest period.

Advantageously, one of the piloting constraints is at least one predetermined time period in the flight that requires a predetermined number of pilots on duty.

The time period is defined between a start time and an end time.

The predetermined number is all the pilots in the crew, for example. Each pilot in the crew must then be on duty during the time period. In particular, this is a "no-sleep" period.

The said predetermined time period is a period of time overflying a predefined geographical area such as a predefined country, for example.

The determination system 10 is thus able to take into account the geopolitical constraints of overflying a territory.

Preferably, one of the piloting constraints is a flight time period that requires a predetermined pilot of the crew pilots on duty. Said predetermined pilot must then be on duty during said time period.

The said predetermined pilot is the captain, for example.

Advantageously, one of the piloting constraints is a parameter representing a tolerance to a current meteorological flight context.

The parameter representing this tolerance is acquired by being reported by a crewmember through the human/machine interface 18, for example.

The weather context comprises an icing condition status, for example. The icing condition status is ice forming on exterior surfaces of the aircraft 12 or within an engine of the aircraft 12.

The weather context includes the turbulence intensity experienced by the aircraft 12 and/or occurrence of a thunderstorm, for example.

The current weather context is provided during flight by sensors on the aircraft 12 and/or by communication with an external control authority, for example.

This allows the crew to choose how weather-sensitive the determined rest scenario will be. For example, it is possible to define that each of the crew pilots must be on duty in the event of an icing condition.

Preferably, the flight context and constraints inputs include at least one pre-flight fatigue parameter for each pilot, representing a pilot-reported pre-flight fatigue state.

The pre-flight fatigue parameter reported by said pilot is acquired by being reported by a crew member through the human/machine interface 18, for example.

The pre-flight fatigue parameter subjectively felt by the pilot is selected by the pilot from a fatigue state scale comprising a plurality of fatigue states, for example.

In one example embodiment, the fatigue state scale includes at least one pre-flight acceptable fatigue state, one pre-flight minor fatigue state, one pre-flight moderate fatigue state and one pre-flight significant fatigue state.

For example, the parameter is obtained from the sum of a first score that represents the number of hours the pilot has slept in the last 24 hours and a second score that represents the number of hours the pilot has slept in the last 48 hours. Based on the calculated sum, the parameter is placed on the fatigue state scale.

Other methods of evaluating the pre-flight fatigue parameter can be chosen and are known to the person skilled in the art.

Advantageously, the flight context and constraints inputs include a post-flight rest parameter for each pilot, representing a rest option for the pilot after landing the aircraft 12 and before any further takeoff.

The determination system 10 is thus suitable for taking into account the subsequent rest options for each pilot in the crew, which may be different from pilot to pilot.

Once the flight context and constraints inputs are acquired by the acquisition module 32, the determination module 34 is configured to determine the crew's rest scenario from said acquired inputs. This determination is made from at least one simulation by a biomathematical fatigue model, having at least one of said acquired inputs as variables, as described in more detail below.

As indicated above, the determination module 34 is configured to be triggered and determine the rest scenario prior to and/or during a flight of the aircraft 12.

Advantageously, the rest scenario is determined for at least a part of the cruise phase of flight.

The rest scenario comprises a rest period(s) schedule, with each period assigned to one of the pilots. The determined rest scenario also comprises one or more duty periods for each pilot.

For each pilot, the pilot's duty periods are contiguous with each pilot's rest period. In the determined rest scenario, each pilot thus preferably alternates one or more duty periods with the determined number of rest periods intended to be provided for this pilot.

To determine the scenario, the determination module 34 is configured to determine at least one rest period(s) chronology compatible with each acquired piloting constraint.

Advantageously, prior to determining each compatible rest period(s) chronology, the determination module 34 is configured to verify at least one compliance condition between at least two of the acquired inputs.

In a preferred example embodiment, the module 34 is thus configured to verify at least one compliance condition, between the available cruise time and the rest periods to be scheduled. More specifically, the compliance condition is then that the available cruise time is sufficiently long to include each rest period, for example.

If the input compliance condition is not met, the determination module 34 is further configured to modify at least one of the acquired inputs, for example, such as at least one of the inputs involved in the compliance condition. The modification is performed such that the compliance condition between modified inputs is met.

In the preferred example, the determination module 34 is configured to reduce the duration of at least one of the rest periods to be provided if the available cruise time is too short to include each rest period. In this case, the determination module 34 advantageously reduces the authorized sleep time while maintaining the predetermined shift transition time.

The determination module 34 is also configured to generate an alert to the crew if at least one of the acquired input compliance conditions is not verified. The alert is also shown, for example, for each input modification made by the determination module 34, if applicable. To do so, the module is preferably configured to generate a signal, such as to the display management module 36, with the signal representing the verification of each compliance condition. The signal also represents each input modification by the determination module 34, if applicable.

In the preferred example, the determination module 34 is configured to generate an alert to the crew if the available cruise time is too short to include each rest period.

Any other acquired input compliance condition may also be checked in this manner.

For the purpose of determining each chronology that is compatible with each acquired piloting constraint, the determination module 34 is configured to discretize the acquired available cruise time down into a plurality of discretized moments, for example. The discretization is done with a predetermined discretized timestep.

As explained in more detail later, the discretized timestep is advantageously determined dynamically, according to the piloting and context constraints.

The discretized timestep is determined by the determination module 34 from computational constraint parameters, for example. The computational constraint parameters are stored in the memory 30, for example.

The computational constraint parameters preferably include a maximum computational time, an estimated computational time per chronology, the number of rest period(s) to be provided, the duration of each rest period and the available cruise time.

The determination of the discretized timestep comprises determination of the maximum number of chronologys to be calculated in order to meet the maximum computational duration constraint from the maximum computational duration and the estimated computational duration per chronology, for example.

The determination of the discretized timestep then comprises determination of the maximum number of time slots per period that make it possible to meet the maximum computational duration constraint.

The determination of the said maximum number is done for example by taking the $n^{th}$ said maximum number of chronologys to be calculated that make it possible to meet the maximum computational duration constraint, where n is the number of rest period(s) to be envisaged.

The determination of the discretized timestep then comprises calculation of the difference between the available cruise time and each rest period duration, and division of this difference by said maximum number of time slots per period, reduced by 1.

The determination of the discretized timestep may also include rounding up the result, for example.

This determination method is not limiting and other methods can be used by the person skilled in the art. In a variant, the discretized timestep can also be set independently of the number of rest period(s) to be provided, the duration of each rest period and the available cruise time, with the timestep then being stored in the memory 30, for example.

After discretization, the determination module 34 is configured to list all the chronologys of rest periods in which each rest period has a start time corresponding to one of the discretized moments.

In each listed chronology, the rest periods all have an end time earlier than or equal to the end of the cruise phase, in particular earlier than or equal to the moment calculated for top of descent.

The module is then configured to verify whether the listed chronology is compatible with each acquired piloting constraint, for each listed chronology.

Thereafter, the determination module 34 is configured to simulate and determine at least one fatigue level of each pilot for each compatible chronology, by the biomathematical model, having at least one of said acquired inputs as variables.

Any chronology that is incompatible with at least one of the acquired piloting constraints is excluded and will not be simulated by the biomathematical model.

The biomathematical model for fatigue (or drowsiness) is suitable for quantifying a fatigue level on a predetermined fatigue scale.

The fatigue level associated to the fatigue scale reflects individual neurobehavioral capabilities such as attention, alertness or sleepiness.

In other words, within the meaning of the present disclosure, the "fatigue level" terms are synonymous with "awake level", "attention level", "alertness level" or "sleepiness level".

Thus, when the determination module 34 simulates and determines a fatigue level, the module provides a quantification of that fatigue level.

The biomathematical model may include a set of equations having said context and flight stress inputs as variables.

The set of equations is thus suitable for producing said fatigue level quantification.

The formula and parameters of each equation may be determined empirically and are advantageously validated for the aeronautical domain.

In one embodiment, the biomathematical model has each pre-flight fatigue parameter reported acquired, in particular, as a variable.

Advantageously, the biomathematical model takes sleep inertia into account in the set of equations. Sleep inertia is defined as a period of altered alertness during the transition from sleep to wakefulness. This period can last from a few minutes to a few hours.

The biomathematical model can preferably take into account each pilot's circadian arrhythmia (also called "jet lag"). Circadian arrhythmia is defined as a physiological condition that results from a previous flight across multiple time areas. Such a flight effectively shifts the various internal clocks (circadian rhythm or sleep cycles) of the individual.

The biomathematical model is the Sleep Wake Predictor (SWP), for example. This biomathematical model is an open-source model, making it possible to predict theoretically and to quantify an individual wakefulness level according to the Karolinska Sleepiness Scale (KSS), developed by the Karolinska Institute in Stockholm.

Other biomathematical models are known to the person skilled in the art and will not be described in more detail here.

After simulation, the determination module 34 is configured to classify each compatible chronology according to an order relationship established from the simulated fatigue levels determined by the model.

The order relationship is a formula that has variables, for example, with each variable having a predetermined weighting. The variables include at least the simulated fatigue levels.

Advantageously, the order relationship is chosen to classify the chronologies by minimizing crew fatigue for landing and/or minimizing each pilot's fatigue during their duty periods.

In a variant or additionally, the order relationship is chosen advantageously to classify the chronologies to facilitate each pilot falling asleep at the beginning of each of his/her rest periods.

In a variant or additionally, the order relationship is chosen to classify the chronologies according to any other fatigue level indicator of each pilot during the timeline.

Advantageously, the determination module 34 is thus configured to simulate and determine, by the biomathematical model and for each compatible timeline, a maximum fatigue level for each pilot on duty during each rest period of each other pilot and/or a fatigue level at a calculated top of descent time TOD of the aircraft 12 of at least each pilot scheduled to be on duty at said time.

Thus, advantageously, the order relationship is established on at least one of said maximum simulated fatigue levels and/or at least one simulated fatigue level at the calculated top of descent time.

In a non-limiting embodiment, the order relationship involves the average of said maximum simulated fatigue levels of each pilot on duty and the average of said fatigue levels at the TOD in each compatible timeline, for example.

In a variant or additionally, the order relationship is advantageously chosen to classify the chronologies by minimizing the fatigue of a predetermined pilot within the crew.

For example, the order relationship is thus established according to the characteristic information of each pilot, namely according to their ages and/or hierarchical status within the crew in particular.

The order relationship is also established according to the acquired post-flight rest parameters, for example.

Each weighting of the order relationship formula is chosen to classify chronologies by minimizing each fatigue level simulated at the moment calculated for the top of descent, for example.

The rest scenario determined by the determination module 34 is then the scenario comprising the compatible timeline that has the best classification according to said order relationship. Once the scenario is determined, the determination module 34 is preferably configured to generate a signal, to the display management module 36, for example, with the signal representing the determined scenario.

Preferably, the determination module is also configured to simulate and determine, by the biomathematical model, each pilot's fatigue level evolution over each pilot duty cycle in the determined rest scenario.

The evolution is a plurality of fatigue levels over time, for example.

Advantageously, the determination system 10 is also configured to send a signal representing the determined rest scenario to the aircraft onboard system 12.

Thereafter, the display management module 36 is configured to display the determined rest scenario on the screen 20 of the display device 16.

After this is displayed, it is possible for the pilot to restart the rest scenario determination. This determination is restarted during flight, for example, based on the development of the mission if the mission differs from its pre-flight forecast, for example.

The acquisition module 32 is then able to acquire new flight context and constraint inputs, with at least one of said inputs being different from the inputs previously acquired to determine the previously displayed scenario.

The determination module 34 is then able to determine at least one new rest scenario from at least one simulation by a biomathematical fatigue model that has at least one of said newly acquired inputs as variables.

The new rest scenario is displayed on the screen 20 of the display device 16 by the display management module 36.

An example of managing the display on the screen 20 of the display device 16, by the display management module 36, will now be described in reference to FIGS. 2 and 3.

Figure 2:
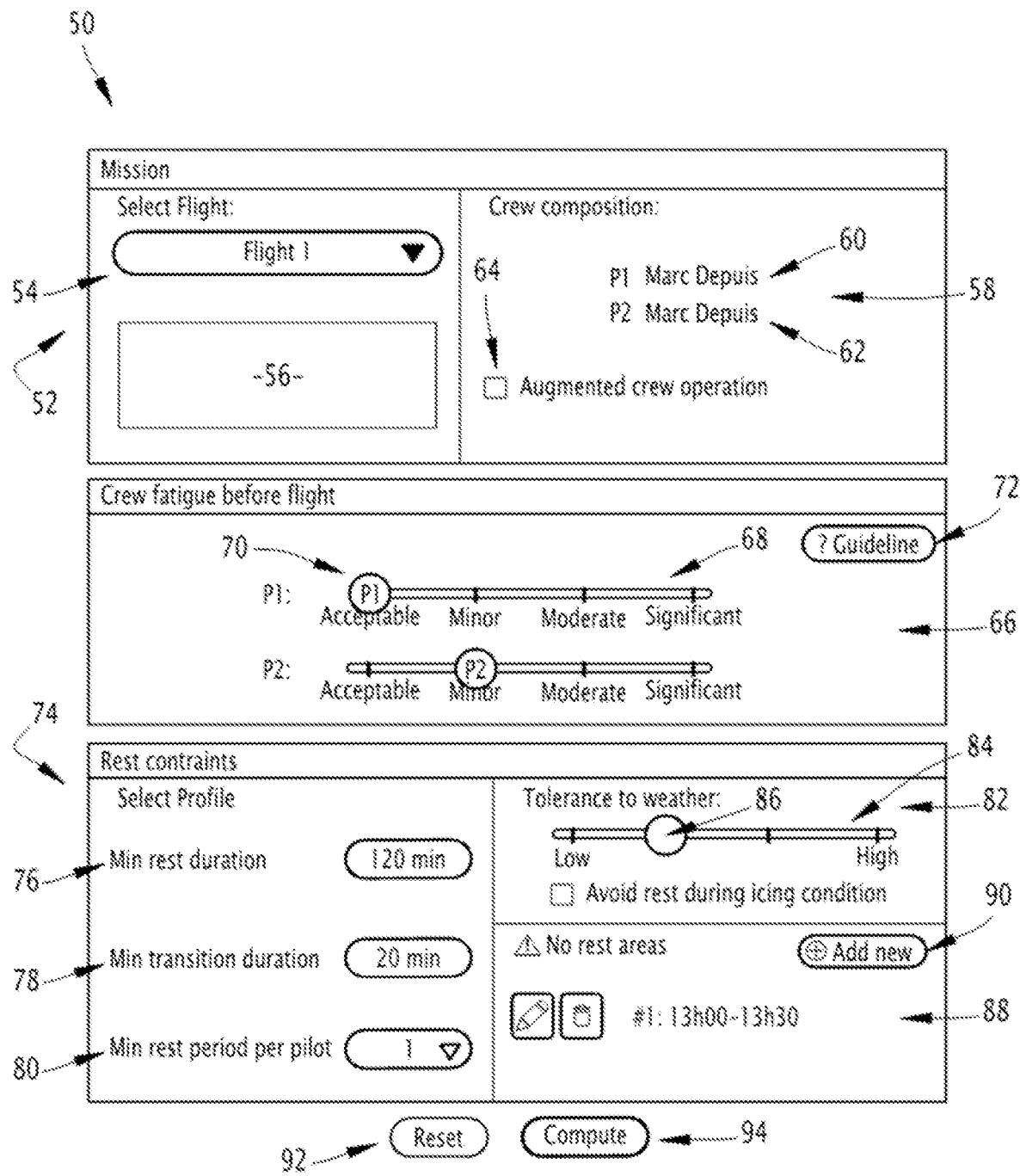
FIGS. 2 and 3 are examples of an input acquisition window and a results window, respectively, displayed by the determination system of FIG. 1.
Figure 3:
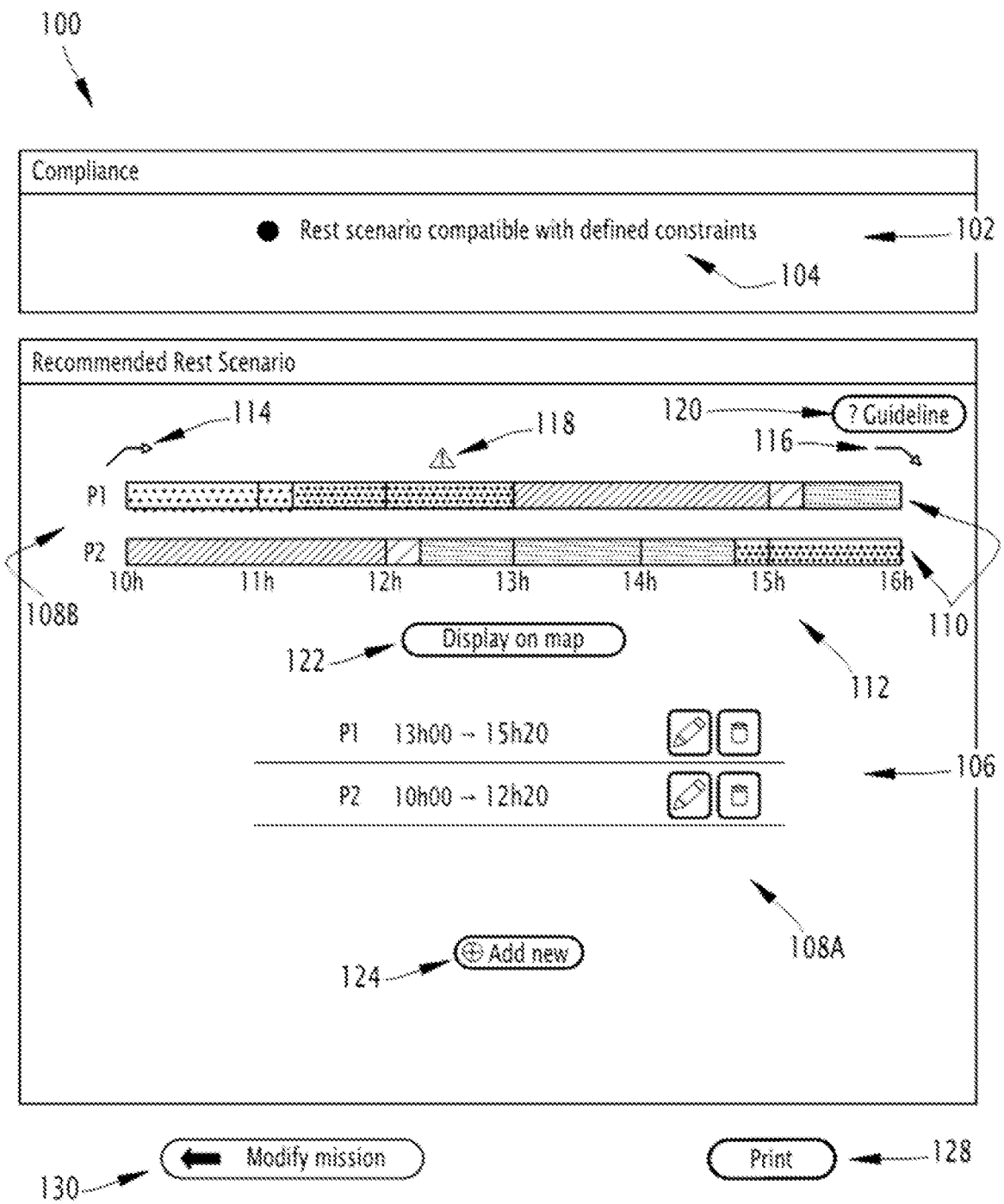

In FIGS. 2 and 3, the annotations are in English, as these figures aim at reproducing a typical example of a graphical interface. The translations of the illustrated English terms will be indicated in the text below.

For the purpose of acquiring at least part of the flight context and constraint inputs, the display management module 36 is configured to display an acquisition window 50 on the screen 20 of the display device 16, a non-limiting embodiment of which is illustrated in FIG. 2.

The window 50 comprises a plurality of graphical input acquisition areas.

The acquisition module 32 is then configured to acquire at least some of the flight context and constraint inputs by the action of graphical elements displayed in each graphic acquisition area.

The action is implemented through the human/machine interface 18.

In the preferred embodiment of a touch screen, the action is detected by the contact of said displayed graphical elements by one or more control members on the surface of the screen 20.

Each input acquisition graphical area is associated to at least one of the flight context and constraint inputs.

Each graphical area preferably has the shape of a frame.

Each graphical area comprises a title representing the input(s) associated with the area, for example, with the title arranged in a respective frame opposite the area. In a variant, the graphical area has no title.

The acquisition window 50 is not limited to the embodiment illustrated in FIG. 2 and described below. In particular, it may include any other graphic acquisition area of other input(s).

One of the graphic acquisition areas displayed is a flight selection area 52. The flight selection area 52 is entitled "Select Flight" here, for example.

A crew member is able to select a flight from among the flights stored in the memory 30. In particular, the selection is made via the human/machine interface 18, by activating a graphical element 54 of the area 52.

When the graphical element 54 is actioned, the display management module 36 displays a list of flights stored in the memory 30 in the form of an actionable drop-down menu.

The flight selection area 52 also displays at least a part 56 of the information about said selected flight that is stored in memory 30.

One of the graphic acquisition areas displayed is a crew composition area 58. The crew composition area 58 is entitled "Crew composition" here, for example.

The crew composition area 58 displays a list 60 of pilots in the crew and at least a part 62 of the characteristic information of each pilot in the crew.

The crew composition area 58 is suitable for adding a new pilot to the displayed list 60. To do so, the area 58 preferably comprises an actionable add icon 64, entitled "Augmented crew operation" here, for example.

In the example embodiment shown in FIG. 2, the flight selection area 52 and the crew composition area 58 are grouped together in a single graphical area, entitled "Mission" here, for example.

One of the graphic acquisition areas is an area 66 of information on the pre-flight fatigue state before flight. The area 66 of information on the fatigue state before flight is entitled "Crew fatigue before flight" here, for example.

As illustrated in FIG. 2, the information area 66 comprises a fatigue state scale 68 for each pilot, for example. Through the fatigue state scale 68, each pilot's pre-flight fatigue parameter may be reported.

In particular, the fatigue state scale 68 is graduated, with each graduation corresponding here to an acceptable pre-flight fatigue state ("Acceptable"), a minor pre-flight fatigue state ("Minor"), a moderate pre-flight fatigue state ("Moderate") and a significant pre-flight fatigue state ("Significant"), for example.

The parameter is reported by the pilot by moving a graphical element 70 on one of the graduation of the fatigue state scale 68 displayed, with the movement made through the human/machine interface 18.

The information area 66 preferably comprises an actionable help icon 72, entitled "? Guideline" here, for example. When the help icon 72 is actioned, the display management module 36 is configured to display help and guidance information on assessing the pre-flight fatigue state to the pilot.

One of the graphic acquisition areas is a rest selection area 74.

The rest selection area 74 comprises a space 76 for selecting the sleep time authorized for each rest period, a space 78 for selecting the shift transition time and a space 80 for selecting the number of rest period(s) per pilot, for example.

Each respective selection is made via the human/machine interface 18 by activating a respective graphical element of each space 76, 78, 80.

When the graphical element of the space 76 for selection of the authorized sleep duration is actioned or when the graphical element of the space 78 for the selection of the transition duration is actioned, the display management module 36 displays a list of proposed durations, in the form of an actionable drop-down menu, or displays a window, for manual input of the duration.

When the graphical element of the space 80 for selecting the number of rest periods per pilot is actioned, the display management module 36 displays a list of proposed numbers, in the form of an actionable drop-down menu, or displays a window, for manual input of the number.

One of the graphic acquisition areas is a weather tolerance area 82, entitled "Tolerance to weather" here, for example.

As illustrated in FIG. 2, the tolerance area 82 comprises a tolerance scale 84, through which the crew member can report the piloting constraint formed by said parameter, representing a tolerance to a current meteorological flight context, for example.

The tolerance scale 84 is graduated, with each graduation corresponding to different tolerances. The tolerance scale 84 comprises at least two end graduations, corresponding to a respective low ("Low") and high ("High") tolerance.

A crew member is able to activate a graphical element 86 associated with the icing condition. This graphical element 86 is entitled "Avoid rest during icing condition" here, for example.

When this graphical element 86 is actioned, no tolerance is associated with the icing condition. In particular, each pilot must then be on duty during icing conditions.

One of the graphic acquisition areas is an area 88 on duty time constraints, entitled "No rest areas" here, for example.

As illustrated in FIG. 2, the duty time constraints area 88 includes an add icon 90, for example, by the actioning of which the crew member can report the piloting constraint formed by a predetermined temporal or geographical area of flight requiring a predetermined number of pilots, such as all, on duty.

The area 88 of temporal or geographical duty constraint includes icons for modifying and deleting the temporal area reported, for each temporal area reported.

The acquisition window 50 also comprises a graphical reset icon 92, entitled "Reset" here, for example.

When a crew member operates the graphical reset icon 92, the display management module 36 is configured to display the acquisition window 50 in a default configuration having default values for each display area, for example. Said default values are stored in the memory 30, for example.

The acquisition window 50 also comprises an actionable graphical icon 94 for triggering determination of the rest scenario, entitled "Compute" here, for example.

Once a crew member actions the graphical trigger icon 94, the acquisition module 32 is configured to acquire each of the flight context and constraint inputs from the graphic acquisition areas of the window 50. The acquisition module 32 is also configured to acquire other inputs by interrogating the memory 30 and/or via sensors of the aircraft 12. The determination module 34 is then configured to determine the rest scenario from the acquired inputs, as explained in more detail above.

Then, the display management module 36 is at least configured to display the determined rest scenario on the display 20 of the display device 16 in a results window 100, a non-limiting embodiment of which is illustrated in FIG. 3.

The results window 100 comprises a plurality of graphical results areas.

The results window 100 comprises actionable graphical elements, for example, with the action implemented via the human/machine interface 18.

The graphical elements are actionable independently of each other.

In the preferred embodiment of a touchscreen, the action is detected by contact of said displayed graphical elements by one or more control members on the surface of the screen 20.

Each graphical results area preferably has the shape of a frame.

Each graphic results area comprises a title representing the result(s) associated with the area, for example, with the title arranged in a respective frame opposite the area. In a variant, the graphical area has no title.

The results window 100 is not limited to the embodiment illustrated in FIG. 3 and described below. In particular, it may comprise any other graphical area.

One of the graphical results areas is an alert area 102 informing of the compliance of inputs acquired, entitled "Compliance" here, for example.

In the alert area 102, the display management module 36 is configured to generate a graphical representation 104 of the alert generated by the determination module 34 in the event that an acquired input compliance condition is not verified. To do so, the display management module 36 is configured to receive the signal representing verification of each compliance condition, which is generated by the determination module 34.

The displayed alert 104 also represents each input modification made by the determination module 34, if any, for example.

The displayed alert 104 is in the form of a text message and/or a colored graphical element, for example.

In the alert area 102, the display management module 36 is also advantageously configured to display a text message and/or colored graphical element in the event that each acquired input compliance condition is verified.

In the example shown in FIG. 3, each compliance condition is verified, with the area 102 displaying a green colored graphical element and the text message "Rest scenario compatible with defined constraints".

One of the graphical result areas is a defined rest scenario area 106, entitled "Recommended Rest Scenario" here, for example.

In the scenario area 106, the display management module 36 is configured to show at least one graphical representation of the determined scenario including the compatible timeline that has the best classification according to said order relationship.

Several embodiments of the graphical representation 108A, 108B of the determined scenario will be described.

In a first embodiment 108A shown in FIG. 3, the graphical representation 108A of the determined scenario comprises the start time and end time of each rest period for each pilot in the crew.

The first embodiment of the graphical representation 108A also comprises a graphical identifier for each pilot, representing the pilot with which each rest period is associated.

In a second embodiment 108B, also shown in FIG. 3, the graphical representation 108B of the determined scenario comprises a timeline 110 for each pilot of the crew, for example, on which each duty period and each rest period of the determined scenario is displayed.

The second graphical representation mode 108B comprises at least one timescale 112 arranged opposite the timelines 110.

The timescale 112 is graduated, with each graduation corresponding to a moment of the flight. In the illustrated example, each graduation is separated by one hour.

The periods in relation to the timescale 112 are placed on each timeline 110 according to their respective start and end times.

The second graphical representation mode 108B also comprises a graphical identifier for each timeline 110, representing the pilot with which said timeline 110 is associated. The identifier is arranged opposite the associated timeline 110.

Advantageously, the authorized sleep time and shift transition time are displayed differently.

In the example of FIG. 3, the authorized sleep time is illustrated by a part of the timeline 100 with a high hatch density and the shift transition time is illustrated by a part of the timeline 100 with a lower hatch density.

Advantageously, the second graphical representation mode 108B of the determined rest scenario represents each pilot's fatigue level evolution over each pilot duty period.

The second graphical representation mode 108B then comprises a color gradient for each duty period displayed, representing said evolution over the duty period, for example.

In the example of FIG. 3, said evolution has been illustrated by a change in dotted line density.

The second graphical representation mode 108B also comprises graphical elements representing at least one of the acquired flight context and constraint inputs, arranged along at least one of the time lines 110, for example.

Advantageously, these graphical elements represent at least some of the acquired flight-associated information. Thus, in the example shown in FIG. 3, the graphical representation 108B of the determined scenario comprises a graphical element 114 representing the top of climb and a graphical element 116 representing the top of descent.

The determined scenario graphical representation 108B also comprises a graphical element 118 representing one of the events intended to occur during the flight, one of the predetermined flight time periods requiring a predetermined number of pilots on duty and/or representing one of the flight time periods requiring a predetermined pilot on duty from among the crew pilots, for example.

The scenario area 106 preferably comprises an actionable help icon 120, entitled "? Guideline" here, for example. When the help icon is actioned, the display management module 36 is configured to display information to assist in reading the display, with the information including descriptions of each graphical element displayed and available commands with descriptions of their effects, for example.

In a third embodiment, not shown, the graphical representation of the determined rest scenario comprises a geographic map flown over during the flight and a flight path of the aircraft 12 over the map, with each rest period of the determined scenario chronology displayed overlaid on the flight path.

The flight path extends between takeoff and landing, for example, or between a current time during the flight and landing.

The periods are placed on the flight path according to their respective start and end times.

Each period then shows a graphical identifier representing the pilot to whom said period is associated, for example.

In addition, advantageously, the third graphical representation mode also represents each pilot's fatigue level evolution over each pilot duty period.

Preferably, the display management module 36 is configured to switch from one display mode, comprising at least one graphical representation of the rest scenario in one of the embodiments described above, to another display mode. comprising at least one graphical representation of the scenario in another embodiment.

In the example shown in FIG. 3, the display management module 36 is configured to switch from a display mode comprising graphical representations of the rest scenario according to the first and second embodiments to another display mode comprising a graphical representation of the scenario according to the third embodiment.

To this end, the rest scenario area 106 preferably comprises a map display icon 122, entitled "Display on map" here, for example. When the display icon 122 is actioned, the display management module 36 is configured to display the graphical representation of the determined scenario according to the third embodiment described above.

Additionally, the crew may manually modify the scenario determined by the determination module 34.

The display management module 36 is thus configured to detect an action of modification of the displayed rest scenario implemented by an operator through the human/machine interface 18 and to modify the display accordingly.

The action of modifying the displayed rest scenario comprises an addition and/or deletion of a rest period in the determined rest scenario, for example.

To do so, in the example illustrated in FIG. 3, the rest scenario area 106 comprises an add icon 124, here entitled "Add new". When the add icon 124 is actioned, the display management module 36 is configured to display a window allowing the operator to manually define a new rest period to be added to the determined rest scenario.

Additionally, in the illustrated example of FIG. 3, the rest scenario area 106 also comprises a delete icon 126. When the delete icon 126 is pressed, the display management module 36 is configured to select and delete one of the rest periods in the determined scenario.

The act of modifying the displayed rest scenario includes changing a position in time of at least one of the rest periods of the scenario, for example.

To do so, the modification action comprises a movement of a member by an operator on the touch screen in a direction substantially parallel to the timescale 112, for example, with the member contacting the screen 20 opposite the rest period to be modified.

Thus, the rest period to be modified is moved in time on the associated time line 110. In particular, it is moved upstream or downstream of the flight, depending on the direction of movement of the member.

At the end of this movement in time, the modified rest period comprises a modified start and end time.

After modification, in particular after addition, deletion and/or movement in time, the determination module 34 is then able to simulate and determine a fatigue level for each pilot in the modified time frame of the modified rest scenario from the biomathematical fatigue model.

Then, the display management module 36 is configured to display the modified rest scenario according to a specific graphical representation. This specific graphical representation is according to one of the embodiments described above, for example.

The results window 100 also comprises an actionable graphical print icon 128, entitled "Print" here, for example, When a crewmember actions the print icon 128, the display management module 36 is configured to initiate a hard copy printout representing the results window 100. This is printed out by the aircraft's printer 12, for example.

In addition, the results window 100 also comprises an actionable graphical return icon 130, for example, entitled "Modify mission" here, for example. When a crew member actions the graphical return icon 130, the display management module 36 is configured to display the acquisition window 50 in place of the results window 100.

In one example of use, after obtaining a first pre-flight results window 100, the graphical return icon 130 may be actioned during flight to restart determination of the scenario based on the development of the mission, advantageously if the mission differs from its pre-flight forecast, for example.

Figure 4:
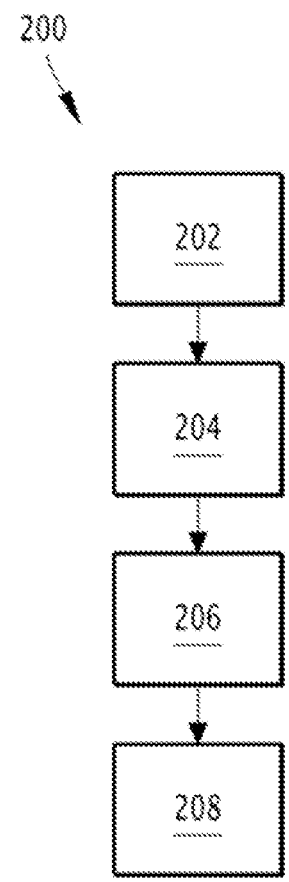
FIG. 4 is a schematic flowchart of a determination method according to an example embodiment of the present disclosure.

A method 200 for determining a flight rest scenario for an aircraft crew 12 will now be described with reference to FIG. 4. Preferably, the method 200 uses the determination system 10 as described above.

The method 200 will be illustrated by several examples.

The method 200 comprises a step 202 of acquiring flight context and constraint inputs, such as those described above.

The acquisition step 202 is implemented by the acquisition module 32 described above, for example.

In a first illustrative example, the method 200 is implemented prior to the top of climb TOC, in particular prior to the flight.

In the first illustrative example, the acquired inputs are specifically those illustrated in FIG. 2. The inputs include:
- a calculated moment for top of climb TOC during the flight occurring at 10:00,
- a calculated moment for top of descent TOD during the flight occurring at 16:00,
- an available cruise time, which is equal to 6 hours here,
- a number of pilots on the crew equal to 2, with the pilots designated hereafter as P1 and P2,
- a pre-flight fatigue state reported as acceptable for pilot P1; a pre-flight fatigue state reported as minor for pilot P2,
- a rest period duration equal to 2 hours 20 minutes, of which 2 hours of authorized sleep time and 20 minutes of shift transition time,
- a number of rest periods to be planned for each pilot equal to 1, this number being the same for each pilot, the number of necessary rest periods to be planned for the crew thus being equal to 2,
- an intermediate tolerance to a current meteorological context,
- a flight time period requiring the two pilots on duty between 12:30 and 13:00.
- the minimum required number of pilot(s) on duty at the controls of the aircraft 12 at each moment of the cruise is equal to 1.

After the acquisition step 202, the method 200 comprises a step 204 of verifying at least one compliance condition between at least two of the acquired inputs.

In the first example, this step 204 specifically verifies that the available cruise time is long enough to include each rest period.

This condition is verified here in that the sum of each rest period durations (4 hours 40 minutes) is less than the available cruise time (6 hours).

No alert is therefore generated in this first example.

The method 200 then comprises a step 206 of determining the crew's rest scenario for the flight from said acquired inputs, with said step 206 implemented by the determination module 34 described above, for example.

As explained in more detail below, this determination is made from at least one simulation by the biomathematical fatigue model, having at least one of said acquired inputs as variables.

The scenario determination step 206 comprises determination of at least one chronology of rest period(s) compatible with each piloting constraint acquired.

For this, the acquired available cruise time is broken down into a plurality of discretized moments, with a predetermined discretized timestep.

For example, the discretized timestep is calculated for calculation constraint parameters comprising a maximum calculation duration of 5 seconds, a calculation duration per chronology estimated at 0.1 second, a number of rest period(s) to be provided equal to 2, each rest period duration equal to 2 hours 20 minutes and the available cruise duration equal to 6 hours.

The maximum number of chronologies to be calculated in order to respect the maximum calculation time constraint is therefore 50 (5 seconds divided by 0.1 second).

The maximum number of temporal positions per period making it possible to meet the maximum duration constraint calculated is thus approximately 7 (the square root of 50).

For a 6 hour cruise and a 2 hours 20 minutes rest time, this gives a discretized timestep of (6 hours–2 hours 20 minutes)/(7–1)=~0.6 hours, or about 36 minutes.

For simplicity in this example, the discretized timestep is rounded up to the next hour and will be considered here as 1 hour.

The determination step 206 subsequently comprises listing all chronologies of rest periods in which each rest period has a start time corresponding to one of the discretized moments. In each listed chronology, the periods in the listed chronology all have an end time prior to the end of the cruise phase, in particular prior to the calculated top of descent time.

With a discretized timestep equal to 1 hour, the chronologies listed in the first example thus include only periods having 10:00, 11:00, 12:00 and 13:00 as the start time. In particular, the chronologies listed here are collated in Table 1 below.

TABLE 1

Timelines listed in the illustrative example

| P1 | P2 |
|---|---|
| 10:00-12:20 pm | 10:00-12:20 pm |
| 10:00-12:20 pm | 11:00-1:20 pm |
| 10:00-12:20 pm | 12:00 pm-2:20 pm |
| 10:00-12:20 pm | 1:00 pm-3:20 pm |
| 11:00-1:20 pm | 10:00-12:20 pm |
| 11:00-1:20 pm | 11:00-1:20 pm |
| 11:00-1:20 pm | 12:00 pm-2:20 pm |
| 11:00-1:20 pm | 1:00 pm-3:20 pm |
| 12:00 pm-2:20 pm | 10:00-12:20 pm |
| 12:00 pm-2:20 pm | 11:00-1:20 pm |
| 12:00 pm-2:20 pm | 12:00 pm-2:20 pm |
| 12:00 pm-2:20 pm | 1:00 pm-3:20 pm |
| 1:00 pm-3:20 pm | 10:00-12:00 pm |
| 1:00 pm-3:20 pm | 11:00-1:20 pm |
| 1:00 pm-3:20 pm | 12:00 pm-2:20 pm |
| 1:00 pm-3:20 pm | 1:00 pm-3:20 pm |

The scenario determination step 206 then comprises verifying whether the listed chronology is compatible with each acquired piloting constraint, for each listed chronology.

In the illustrated example, the piloting constraints considered are in particular the flight time period requiring the two pilots on duty between 12:30 pm and 1:00 μm, and the minimum number of pilot(s) required on duty at the controls of the aircraft 12 at each moment of the cruise as equal to 1. In other words, the rest periods cannot overlap.

Thus, the chronologies listed as compatible here are collated in Table 2 below.

TABLE 2

Timelines listed as compatible in the illustrative example

|  | P1 | P2 |
|---|---|---|
| Timeline 1 | 10:00-12:20 pm | 1:00 pm-3:20 pm |
| Timeline 2 | 1:00-3:20 pm | 10:00-12:20 pm |

The determination step 206 then comprises simulating and determining at least one fatigue level of each pilot, for each compatible chronology, by the biomathematical model.

Advantageously, the determination step 206 comprises the biomathematical model simulating and determining, for each compatible chronology, a maximum fatigue level of each pilot on duty during each rest period of each other pilot and/or a fatigue level, at a calculated top of descent (TOD) time of the aircraft 12, of at least each pilot scheduled to be on duty at said time.

The biomathematical fatigue model quantifies each fatigue level on a predetermined fatigue scale. The biomathematical model here is the SWP model.

In the illustrative example, the simulated fatigue levels for each compatible chronology are collated in Table 3 below. "Max P1 fatigue during P2 rest" means the maximum fatigue level of pilot P1 on duty during the rest period of pilot P2. Furthermore, "P1 fatigue at TOD" means the fatigue level of pilot P1 at the calculated top of descent (TOD) time.

TABLE 3

Simulated and determined fatigue states for each compatible timeline in the illustrative example

| | P1 | P2 | Max P1 fatigue during P2 rest | Max P2 fatigue during P1 rest | P1 Fatigue at TOD | P2 Fatigue at TOD |
|---|---|---|---|---|---|---|
| Timeline 1 | 10:00-12:20 pm | 1:00 pm-3:20 pm | 5.8 | 4.1 | 4.8 | 4.5 |
| Timeline 2 | 1:00-3:20 pm | 10:00-12:20 pm | 5 | 5.5 | 4 | 5.2 |

After simulation, the determination step 206 comprises classification of each compatible chronology according to an order relationship established from the simulated fatigue levels.

For example, the order relationship here involves the average of said simulated maximum fatigue levels of each pilot on duty and the average of said fatigue levels at the TOD, within each compatible chronology.

The order relationship then comprises a weighted average of the rankings obtained.

In the illustrative example, the weighting of the associated ranking for the fatigue levels at the TOD is twice that of the associated ranking for the maximum simulated fatigue levels of each pilot on duty.

In the illustrative example, the rankings obtained are collated in Table 4 below.

TABLE 4

Rankings obtained in the illustrative example

| | Max P1 fatigue during P2 rest | Max P2 fatigue during P1 rest | Average | Ranking | P1 Fatigue P1 at TOD | P2 Fatigue at TOD | Average | Ranking | Overall Ranking (weighting of rankings) |
|---|---|---|---|---|---|---|---|---|---|
| Timeline 1 | 5.8 | 4.1 | 4.95 | 1 | 4.8 | 4.5 | 4.65 | 2 | 1.67 |
| Timeline 2 | 5 | 5.5 | 5.25 | 2 | 4 | 5.2 | 4.6 | 1 | 1.33 |

At the end of the determination step 206, the determined rest scenario comprises the compatible chronology that has the highest ranking according to the order relationship.

In the illustrative example, the best ranking is the chronology with the lowest "overall ranking" to minimize fatigue.

The determined scenario in this example thus comprises the numbered chronology 2, and thus comprises a rest period for pilot P2 between 10:00-12:20 µm and a rest period for pilot P1 between 1:00-3:20 µm.

The method 200 then comprises a step 208 of displaying the determined rest scenario on the screen 20 of the display device 16.

This display step 208 is implemented by the display management module 36 described above, for example.

In particular, FIG. 3 shows a graphical representation of the scenario determined in the illustrative example.

A second illustrative example of the method 200 will now be described.

In the second illustrative example, the method 200 is implemented during cruise at a current time. In the second example, the pilot P2 here has had a rest period prior to this current time.

The inputs acquired for the second example thus differ from those of the first in that the available cruise time corresponds to the difference between the current flight time and the calculated top of descent TOD time.

The inputs acquired for the second example thus include:

the current time occurring at 2:00 pm, i.e. before the calculated top of descent TOD time occurring at 4:00 pm, an available cruise time of 2 hours, a number of rest periods to be provided for the pilot P1 equal to 1 and number of rest periods to be planned for the pilot P2 equal to 0, with the number of rest periods required to be planned for the crew thus being equal to 1.

The other inputs acquired for the second example are similar to those of the first illustrative example.

After the acquisition step 202, the method 200 comprises the step 204 of verifying the compliance condition that the available cruise time is long enough to include each rest period.

In the second example, this condition is not verified, in that the duration of the only rest period to be provided (2 hours 20 minutes) is greater than the available cruise duration (2 hours).

The method 200 therefore comprises generating an alert to the crew and modifying the acquired rest period duration.

In this case, the authorized sleep time of the rest period is reduced while the predetermined shift transition time is maintained.

In the second example, the rest period duration is modified, to be reduced to 2 hours, by reducing the authorized sleep duration to 1 hour 40 minutes and keeping the shift transition duration at 20 minutes.

The scenario determination step 206 comprises determining at least one chronology of rest period(s) compatible with each acquired piloting constraint, but there is only one possible chronology in this case, namely a chronology comprises a rest period for the pilot P1 between 2:00 and 4:00 μm.

The determination step 206 then comprises the simulation and determination of each pilot's fatigue level by the biomathematical model, for said compatible chronology.

After simulation, the determination step 206 comprises said classification, which is direct here in there is only one compatible chronology.

The method 200 then comprises the step 208 of displaying the determined rest scenario on the screen 20 of the display device 16 and displaying a graphical representation of the generated alert. The displayed alert is also shown to indicate the modification of the rest period duration.

Variants and additions to the above determination system will now be described.

In one variant, the crew comprises at least three pilots, such as exactly three pilots. In another variant, the crew includes at least four pilots, such as exactly four.

In one variant, the screen 20 of the display device 16 is non-touchable.

In one variant, the human/machine interface 18 comprises a mouse and a keyboard. The interface 18 is then specifically configured to detect the position of a graphic pointer controlled by the mouse, on a surface of the screen 20.

In another variant, the determination system 10 is not included in the aircraft 12.

In one advantageous variant, not shown, the system onboard the aircraft 12 comprises a wake-up device for a pilot at rest and the wake-up module is configured to actuate the wake-up device.

The wake-up device is adapted to be actioned to wake up one of the pilots when (s)he is in her/his rest period.

The determination system 10 is thus connected to the wake-up device.

The wake-up module is configured to actuate the wake-up device of a rest pilot according to the determined rest scenario.

In particular, the wake-up module is configured to actuate the wake-up device based on an end time of the authorized sleep time of each rest period.

In one variant, not shown, the display management module 36 is configured to further display at least one alternative rest scenario. The alternative rest scenario then comprises the compatible chronology having the second highest classification according to the order relationship.

More generally, the display management module 36 is advantageously configured to further display a predetermined number of alternative rest scenarios, comprising the respective compatible chronologies having the best classifications according to the order relationship.

In another variant, after having determined the compatible chronology having the best classification, the determination module 34 is configured to refine the scenario determination by implementing each step again from the step of discretization of the available cruise time, for example.

Indeed, the fact of having determined the best classification chronology makes it possible to reduce the discretization in that it is no longer necessary to discretize the whole available cruise time and it is possible to only discretize the time windows around each rest period.

More specifically, the determination module 34 is configured to determine a time window including the period having the best classification, for each period of said compatible chronology.

The determination module 34 is then configured to discretize each time window into a plurality of reduced discretized moments, with a reduced discretized timestep.

The reduced discretized timestep is smaller than the predetermined discretized timestep.

After the reduced discretization, the determination module 34 is configured to then list all new chronologies of rest period(s) in which each rest period has a start time corresponding to one of the reduced discretized moments. Each rest period is included in one of said time windows.

The determination module 34 is configured to verify, for each listed new chronology, whether the listed new chronology is compatible with each piloting constraint.

Further, the determination module 34 is configured to simulate and determine, by the biomathematical model and for each new compatible chronology, at least one new fatigue level of each pilot.

Thereafter, the determination module 34 is configured to classify each new compatible chronology according to the order relationship established from the simulated new fatigue levels.

The rest scenario determined by the determination module 34 is then the scenario comprising the new compatible chronology that has the best classification according to said order relationship.

As a result of the previously described features, the determination system 10 allows for improved safety of the aircraft 12 by minimizing crew fatigue during the flight by implementing rest periods.

In particular, the system proposes the most timely and efficient rest scenario possible, while respecting the physiological needs and various flight constraints such as regulatory requirements.

The determination system 10 is robust to the number of pilots and to the addition of any other new minimization criteria.

The determination system 10 also allows crew members to modify the proposed scenario and to visualize the effects of each modification of the crew's fatigue level.

What is claimed is:

1. A system for determining an in-flight rest scenario for a crew of an aircraft, the crew comprising at least two pilots able to fly the aircraft during a flight of the aircraft, the system comprising:
   a display device comprising a screen;
   an acquisition module configured for acquiring flight context and constraints inputs, the flight context and constraints inputs comprising at least one piloting constraint on piloting by the crew of the aircraft;
   a determination module configured for determining at least one in-flight rest scenario for the crew from the acquired flight context and constraints inputs, the determination module being configured to determine the in-flight rest scenario from at least one simulation by a biomathematical fatigue model having at least one of the acquired flight context and constraints inputs as variables;

a human/machine interface configured to receive interactions of a user, the interactions being input by a keyboard, a mouse and/or a touch control device configured for detecting the position on a surface of the touch control device of one or more members; and a display management module configured to:
  display an input acquisition window on the screen of the display device, comprising a plurality of graphical input acquisition areas, each graphical input acquisition area being associated to at least one of the piloting constraints, the acquisition module being configured to acquire at least one of the piloting constraints by a user activating graphical elements displayed on the screen of the display device in each graphical input acquisition area via the human/machine interface,
  in response to at least one of the interactions via the human/machine interface with at least one of the graphical elements displayed on the input acquisition window:
    determine at least two candidate chronologies, each candidate chronology including at least one rest period being compatible with each piloting constraint and being assigned to one of the pilots, each candidate chronology further including, for each pilot, at least one duty period for the pilot, the two candidate chronologies extending over a same time frame of the flight of the aircraft,
    simulate and determine at least one fatigue level of each pilot, for each compatible candidate chronology, by the biomathematical model,
    classify each compatible candidate chronology according to an order relationship established from the simulated fatigue levels,
  display a results windows on the screen of the display device, comprising a rest scenario graphical area including a graphical representation of the determined in-flight rest scenario determined for a cruise phase of flight, the graphical representation of the determined in-flight rest scenario comprising at least two timelines, one for each pilot, at least one timescale arranged opposite the timelines, and a graphical representation of the at least one rest period of the compatible candidate chronology that has a best classification according to the order relationship being placed on at least one of the two timelines, the graphical representation of the determined in-flight rest scenario comprising, for each of the at least one rest period, a graphical information representative of the starting time and/or a graphical information representative of the end time of the rest period assigned to the pilot displayed along a timescale indicating a time period of the flight,
  receive an input by the user, via the human/machine interface, to modify at least one of the piloting constraints inputs by at least one of the interactions of the user with at least one of the activated graphical elements displayed on the screen of the display device, and
  in response to the at least one interaction of the user with at least one of the activated graphical elements displayed on the screen of the display device, modifying a position in time of at least one of the rest periods within at least one of the timelines by displaying the graphical information representative of the starting time and/or the graphical information representative of the end time of the rest period assigned to the pilot at a different position along the timescale.

2. The system according to claim 1, wherein the or one of the piloting constraints is a minimum number of pilot(s) required on duty at each moment of the cruise phase;
and/or the or one of the piloting constraints is a predetermined temporal or geographical area of flight requiring a predetermined number of pilots on duty.

3. The system according to claim 1, wherein the flight context and constraints inputs include at least one pre-flight fatigue parameter for each pilot, representing a pre-flight fatigue state reported by the pilot, the biomathematical model having the pre-flight fatigue parameter as a variable.

4. The system according to claim 1, wherein the determination module is configured to simulate and determine, by the biomathematical model and for each compatible candidate chronology, a maximum fatigue level of each pilot on duty during each rest period of each other pilot and/or a fatigue level at a calculated top of descent time of the aircraft of at least each pilot scheduled to be on duty at the time, the order relationship being established on at least one of the simulated and determined fatigue levels.

5. The system according to claim 1, wherein the flight context and constraint inputs include an available cruise time, a number of required rest period(s) to be provided for the crew, and a rest period duration,
  the determination module being configured to discretize the available cruise time into a plurality of discretized moments, the discretization being done with a predetermined discretized timestep, the discretized timestep being smaller than the available cruise time,
  the determination module being configured to determine each compatible candidate chronology such that each rest period of the compatible candidate chronology has a start time corresponding to one of the discretized moments.

6. The system according to claim 5, wherein the determination module is configured, after discretization, to list all of the chronologies of rest periods in which each rest period has a start time corresponding to one of the discretized moments, and to verify, for each listed chronology, whether the listed chronology is compatible with each piloting constraint thereby determining the compatible candidate chronologies.

7. The system according to claim 6, wherein, after determining the compatible candidate chronology having the best classification, the determination module is configured to determine, for each rest period of the chronology, a time window including the rest period,
  the determination module being configured to discretize, with a reduced discretized timestep, each time window into a plurality of reduced discretized moments, the reduced discretized timestep being smaller than the predetermined discretized timestep,
  the determination module being configured, after reduced discretization, to list all the new chronologies of rest periods in which each rest period has a start time corresponding to one of the reduced discretized moments, and to verify, for each listed new chronology, whether the listed new chronology is compatible with each piloting constraint,
  the determination module being configured to simulate and determine, by the biomathematical model and for each new compatible chronology, at least one new fatigue level of each pilot, the determination module being configured to classify each new compatible chronology, according to the order relationship, established from the new simulated fatigue levels, the determined in-flight rest scenario comprising the new compatible chronology having the best classification according to said order relationship.

8. The system according to claim 1, wherein, before determining each candidate chronology of rest period(s) compatible with each acquired piloting constraint, the determination module is configured to verify at least one compliance condition between at least two of the acquired flight context and constraints inputs, and configured to modify one of the acquired flight context and constraints inputs if the compliance condition between the at least two acquired flight context and constraints inputs is not verified and/or generate an alert for the crew if the compliance condition between the at least two acquired flight context and constraints inputs is not verified, the display management module being configured to generate a graphical representation of the alert.

9. The system according to claim 8, wherein the flight context and constraints inputs include an available cruise time, a number of required rest period(s) to be scheduled for the crew, and a rest period duration; the determination module being configured to verify a compliance condition between the available cruise time and the rest periods to be scheduled, the compliance condition being that the available cruise time is long enough to include each rest period.

10. The system according to claim 9, wherein the determination module is configured to generate an alert to the crew if the available cruise time is too short to include each rest period and/or configured to reduce the duration of at least one of the scheduled rest periods if the available cruise time is too short to include each rest period.

11. The system according to claim 1, wherein each rest period includes an authorized sleep duration and a shift transition duration.

12. The system according to claim 1, wherein the determined in-flight rest scenario also includes duty periods for each pilot, the determination module being configured to simulate and determine, by the biomathematical model, each pilot's fatigue level evolution over each pilot's duty period, the display management module being configured to display a specific graphical representation of the determined in-flight rest scenario representing each evolution, on the screen of the display device.

13. The system according to claim 1, wherein the display management module is configured to detect an action of modification of the displayed in-flight rest scenario implemented by an operator through the human/machine interface to generate a modified in-flight rest scenario,
the determination module being configured to simulate and determine each pilot's fatigue level from the biomathematical fatigue model in the modified in-flight rest scenario, the display management module being configured to display the modified in-flight rest scenario, according to a specific graphical representation.

14. The system according to claim 1, wherein the or one of the piloting constraints is a temporal or geographical area of flight requiring a predetermined pilot on duty from among the pilots of the crew; and/or the or one of the piloting constraints is a parameter showing a tolerance to a current meteorological flight context.

15. The system according to claim 1, wherein each candidate chronology comprises at least two rest periods, each rest period being assigned to a different pilot of the crew.

16. The system according to claim 1, wherein the determined in-flight rest scenario also includes duty periods for each pilot, an order relationship being chosen to classify each candidate chronology by minimizing crew fatigue for each pilot's fatigue during their duty period(s),
and/or the order relationship being chosen to classify each candidate chronology to facilitate each pilot falling asleep at a beginning of each of his/her rest period(s).

17. The system according to claim 1, wherein the input acquisition window comprises an actionable graphical icon, the determination module being configured for determining the in-flight rest scenario upon an actuation of said graphical icon, the actuation being implemented via the human/machine interface.

18. The system according to claim 1, wherein the determined in-flight rest scenario also includes duty periods for each pilot, each duty period and rest period having a start time and an end time, the graphical representation of the determined in-flight rest scenario comprising a timeline for each pilot, each duty period and rest period of said pilot being placed on the timeline according to their respective start time and end time.

19. The system according to claim 18, wherein the results window comprises graphical elements representing at least one of the acquired flight context and constraint inputs, arranged along at least one of the timelines.

20. The system according to claim 1, wherein the graphical input acquisition areas include a fatigue state scale via which a fatigue state parameter is modifiable by the pilot moving a graphical element, via the human/machine interface, on the fatigue state scale.

21. The system according to claim 1, wherein the graphical input acquisition areas include a rest selection area comprising a space for selecting, via the human/machine interface, a sleep time authorized for each rest period, a space for selecting a shift transition time and/or a space for selecting a number of rest period(s) per pilot.

22. The system according to claim 1, wherein the graphical input acquisition areas include a weather tolerance area including a tolerance scale, modifiable via the human/machine interface to report a tolerance to a current meteorological flight context.

23. The system according to claim 1, wherein the graphical input acquisition areas include a duty time constraints area including an icon that is actionable, via the human/machine interface, to report a predetermined temporal or geographical area of flight requiring a predetermined number of pilots on duty.

24. A method for determining an in-flight rest scenario for a crew of an aircraft, the crew comprising at least two pilots able to fly the aircraft during a flight of the aircraft, the method comprising:
displaying an input acquisition window on a screen of a display device, comprising a plurality of graphical input acquisition areas, each graphical input acquisition area being associated to at least one flight context and constraints input,
acquiring flight context and constraints inputs, the flight context and constraints inputs comprising at least one piloting constraint on piloting by the crew of the aircraft, a part of the piloting constraints being acquired by activating graphical elements, via a human/machine interface, displayed on the screen in each acquisition area and actioning, via the human/machine interface, a graphical trigger icon to cause the acquiring of the part of piloting constraints from the graphic acquisition areas of the window and to cause acquiring of another part of the piloting constraints by interrogating a computer memory and/or via sensors of the aircraft, the human/machine interface being configured to receive interactions of a user, the interactions being input by a keyboard, a mouse and/or a touch control device configured for detecting the position on a surface of the touch control device of one or more members;

determining, in response to the actioning of the graphical trigger icon, at least one in-flight rest scenario for the crew from the acquired piloting constraints, the in-flight rest scenario being determined from at least one simulation by a biomathematical fatigue model, having at least one of the acquired piloting constraints as variables, the determining the at least one in-flight rest scenario including in response to at least one of the interactions via the human/machine interface with at least one of the graphical elements displayed on the input acquisition window:

determining at least two candidate chronologies, each candidate chronology including at least one rest period being compatible with each piloting constraint and being assigned to one of the pilots, each candidate chronology further including, for each pilot, at least one duty period for the pilot, the two candidate chronologies extending over a same time frame of the flight of the aircraft, simulating and determining at least one fatigue level of each pilot, for each compatible candidate chronology, by the biomathematical model, and classify each compatible candidate chronology according to an order relationship established from the simulated fatigue levels;

displaying a results windows on the screen of the display device, comprising a rest scenario graphical area including a graphical representation of the determined in-flight rest scenario determined for a cruise phase of flight, the graphical representation of the determined in-flight rest scenario comprising at least two timelines, one for each of the pilots, and at least one timescale arranged opposite the timelines, and a graphical representation of the at least one rest period of the compatible candidate chronology that has a best classification according to the order relationship being placed on at least one of the two timelines, the graphical representation of the determined in-flight rest scenario comprising, for each pilot, a graphical information representative of a starting time and/or a graphical information representative of an end time of the rest period assigned to the pilot placed on the respective timeline for the pilot displayed along a timescale indicating a time period of the flight;

receiving an input by a user, via the human/machine interface, to modify at least part of the piloting constraints by an interaction of the user with at least one of the activated graphical elements displayed on the screen of the display device; and in response to the interaction of the user with at least one of the activated graphical elements displayed on the screen of the display device, modifying a position in time of at least one of the rest periods within at least one of the timelines by displaying the graphical information representative of the starting time and/or the graphical information representative of the end time of the rest period assigned to the pilot at a different position along the timescale.

25. The method according to claim 24, wherein receiving the input by the user is performed in the cockpit during the flight of the aircraft.

\* \* \* \* \*